United States Patent
Wuts

(10) Patent No.: US 6,586,595 B2
(45) Date of Patent: Jul. 1, 2003

(54) PROCESS TO PREPARE (5R)-(METHYLAMINO)-5, 6-DIHYDRO-4H-IMIDAZO[4,5,1-IJ]-QUINOLIN-2(1H)-ONE

(75) Inventor: Peter Guillaume Marie Wuts, Mattawan, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/934,749

(22) Filed: Aug. 22, 2001

(65) Prior Publication Data

US 2002/0183520 A1 Dec. 5, 2002

Related U.S. Application Data

(63) Continuation of application No. 09/494,750, filed on Jan. 31, 2000, now Pat. No. 6,355,802.
(60) Provisional application No. 60/118,766, filed on Feb. 5, 1999.

(51) Int. Cl.[7] ............................................. C07D 471/06
(52) U.S. Cl. ............................................ 546/64; 546/84
(58) Field of Search ...................................... 546/64, 84

(56) References Cited

U.S. PATENT DOCUMENTS

| | | |
|---|---|---|
| 5,273,975 A | 12/1993 | Moon et al. |
| 5,652,245 A | 7/1997 | Romero |
| 6,197,339 B1 | 3/2001 | Ju .............................. 424/468 |
| 6,455,564 B1 * | 9/2002 | Meglasson .................. 514/387 |

OTHER PUBLICATIONS

Protective Groups in Organic Synthesis, Wiley & Sons, 1991.
J. Heterocyclic Chem., 19, 837–49 (1982) (copy to be supplemented).

* cited by examiner

*Primary Examiner*—Evelyn Mei Huang
(74) *Attorney, Agent, or Firm*—John H. Engelmann

(57) ABSTRACT

The present invention is an improved prosess to prepare (5R)-(methylamino)-5,6-dihydro-4H-imidazo[4,5,1-ij] quinolin-2(1H)-one the compound of formula (VII)

6 Claims, No Drawings

PROCESS TO PREPARE (5R)-(METHYLAMINO)-5, 6-DIHYDRO-4H-IMIDAZO[4,5,1-IJ]-QUINOLIN-2(1H)-ONE

CROSS REFERENCE TO RELATED APPLICATIONS

This patent application is a continuation of U.S. patent application Ser. No. 09/494,750, filed Jan. 31, 2000, U.S. Pat. No. 6,355,802 which was a continuation of U.S. patent applications Ser. No. 60/118,766, filed Feb. 5, 1999 now abandoned.

BACKGROUND OF THE INVENTION

1. Field of the Invention

The present invention is a process and intermediates to produce a pharmaceutically useful compound, (5R)-(methylamino)-5,6-dihydro-4H-imidazo[4,5,1-ij]quinolin-2 (1H)-one (VII).

2. Description of the Related Art

U.S. Pat. No. 5,273,975 discloses a genus which includes (5R)-(methylamino)-5,6-dihydro-4H-imidazo[4,5,1-ij] quinolin-2(1H)-one. (5R)-(methylamino)-5,6-dihydro-4H-imidazo[4,5,1-ij]quinolin-2(1H)-one (VII) can be made by the process disclosed in U.S. Pat. No. 5,273,975.

U.S. Pat. No. 5,652,245 discloses a process to to produce heterocyclic amines similar to those of U.S. Pat. No. 5,273, 975. In addition, it discloses a process which can be used to make (5R)-(methylamino)-5,6-dihydro-4H-imidazo[4,5,1-ij]quinolin-2(1H)-one (VII).

SUMMARY OF INVENTION

Disclosed is a tricyclic compound of formula (II) where $R_N$ is selected from the group consisting of:
(A) $\phi$-CH$_2$— where phenyl is optionally substituted with 1 or 2: (1) $C_1$-$C_4$ alkoxy, (2) F—, (3) Cl—, (4) Br—, (5) I—, (6) $C_1$-$C_4$ alkyl,
(B) $R_{N1}$—CH$_2$—O—CH$_2$— where $R_{N1}$ is selected from the group consisting of:
 (1) $\phi$-optionally substituted with: (a) $C_1$-$C_4$ alkyl, (b) F—, (c) Cl—, (d) Br—, (e) I—, (f) $C_1$-$C_4$ alkoxy,
 (2) (CH$_3$)$_3$Si—CH$_2$—,
 (3) $R_{N2}$—O—CH$_2$— where $R_{N2}$ is $C_1$-$C_4$ alkyl,
 (4) CH$_2$=CH—,
 (5) —H,
 (6) $C_1$-$C_4$ alkyl;
(C) an unsaturated compound selected from the group consisting of: (1) CH$_2$=CH—CH$_2$—, (2) CH$_3$—CH=CH—CH$_2$— and (3) $\phi$-CH=CH—CH$_2$—.

Also disclosed is a hydroxy compound of formula (III) where $R_N$ is as defined above and where $R_X$ is selected from the group consisting of —Br, —Cl and —I.

Further, disclosed is an ester of formula (IV) where $R_N$ is as defined above.

Additionally disclosed is the hydroxy-amino compound of formula (V) where $R_N$ is as defined above.

Disclosed is the tetracyclic compound of formula (VI) where $R_N$ is as defined above.

DETAILED DESCRIPTION OF THE INVENTION (5R)-(Methylamino)-5,6-dihydro-4H-imidazo[4,5,1-ij] quinolin-2(1H)-one (VII) is known to be useful a a pharmaceuical agent, see U.S. Pat. No. 5,273,975. Because the compound has an enantiomeric center it is difficult to prepare this compound optically pure. One can produce the compound in racemic form and then resolve it by known means.

The invention here is a stereoselective synthetic process to preapre (5R)-(methylamino)-5,6-dihydro-4H-imidazo[4, 5,1-ij]quinolin-2(1H)-one (VII) which produces the desired enantiomer utilizing resolution of diastereomers. The material which is lost, is recycled back to the starting material (1).

The process of the present invention is the same regardless of which of the variable substituents $R_N$ and $R_X$ are utilized with the exception of how the $R_N$ protective group is removed. This is well known to those skilled in the art.

The starting material, 1,2-dihydro-4H-imidazo[5,4-1-ij] quinolin-2-one (I) is known, see J. Heterocyclic Chem., 19, 837-49 (1982). The unsubstituted tricyclic amide (I) is transformed to the corresponding tricyclic amide (II) by means well known to those skilled in the art for transformation of an amide to a substituted amide. The tricylic amide (II) requires the amide nitrogen atom be protected by $R_N$. Operable $R_N$ groups include:
(A) $\phi$-CH$_2$— where phenyl is optionally substituted with 1 or 2:
 (1) $C_1$-$C_4$ alkoxy, (2) F—, (3) Cl—, (4) Br—, (5) I—, (6) $C_1$-$C_4$ alkyl,
(B) $R_{N1}$—CH$_2$—O—CH$_2$— where $R_{N1}$ is selected from the group consisting of:
 (1) $\phi$ optionally substituted with:
  (a) $C_1$-$C_4$ alkyl, (b) F—, (c) Cl—, (d) Br—, (e) I—, (f) $C_1$-$C_4$ alkoxy,
 (2) (CH$_3$)$_3$Si—CH$_2$—,
 (3) $R_{N2}$—O—CH$_2$— where $R_{N2}$ is $C_1$-$C_4$ alkyl,
 (4) CH$_2$=CH—
 (5) —H,
 (6) $C_1$-$C_4$ alkyl;
(C) an unsaturated compound selected from the group consisting of:
 (1) CH$_2$=CH—CH$_2$—, (2) CH$_3$—CH=CH—CH$_2$— and (3) $\phi$-CH=CH—CH$_2$—.

It is preferred that $R_N$ be $\phi$-CH$_2$—.

When the $R_N$ protecting group is $\phi$-CH$_2$— optionally substituted with (A) $\phi$-CH$_2$— where phenyl is optionally substituted with 1 or 2 $C_1$-$C_4$ alkoxy, F—, Cl—, Br—, I— and $C_1$-$C_4$ alkyl, this protecting group is removed by use of metal/ammonia at the same time the aziridine (VI) is opened. When the $R_N$ protecting group is non-benzyl, such as (CH$_3$)$_3$Si—CH$_2$— this group is removed with fluoride ion or strong acid. When the $R_N$ protecting group is non-benzyl, non-silyl, such as $R_{N2}$—O—CH$_2$— where $R_{N2}$ is $C_1$-$C_4$ alkyl this group is removed by Lewis acid such as zinc chloride or Bronsted acid. When the $R_N$ protecting group is an unsaturated non-benzyl, such as CH$_2$=CH— this group is removed by palladium catalysis in the presence of a nucleophile. All of these removal methods are well known to those skilled in the art, see for example, Protective Groups In Organic Synthesis, Wiley & Sons, 1991.

The tricyclic amide (II) is transformed to the corresponding hydroxy compound (III) by reaction with an agent which can produce a halohydrin (III). Suitable agents include dibromantin (or its equivalent with other than bromine when $R_X$ is other than —Br). Operable $R_X$ include —Cl, —Br and —I; it is preferred that $R_X$ be —Br. It is preferred to use an aprotic solvent such as acetonitrile, a catalytic amount of fluoboric acid at a low temperature of about 0°; see EXAMPLE 2.

The optically impure hydroxy compound (III) is reacted with the acid chloride, naproxen chloride (PREPARATION I), to form diastereoisomeric esters (IVA) and (IVB); see EXAMPLE 3. The isomer that will produce the desired product (VII), is ester (IVA), The ester (IVB) is useful because it can be readily transformed back to the tricyclic compound (II), by known means, and be recycled.

The ester (IVA) is then converted to the corresponding hydroxy-amino compound (V) by the process of EXAMPLE 4.

The hydroxy-amino compound (V) is transformed to the corresponding tetracyclic compound (VI) by a multi-step reaction. First the hydroxy-amino compound (V) is contacted with a strong base. Preferred strong bases are alkyl lithium reagents (such as butyllithium, methyllithium), potassium hexamethyldisilazide and lithium diisopropylamide. Following the contacting with a strong base, the reaction mixture of step (1) is contacted with a compound of the formula $R_S$—$SO_2$—X where $R_S$ is phenyl and substituted phenyl and where X is —Cl or —Br. It is preferred that $R_S$ is phenyl or tolyl. The final step is quenching with a weak base. Suitable weak bases include bicarbonate, carbonate, (phosphate) buffers and hydroxide; preferred is bicarbonate. The preferred process is exemplified in EXAMPLE 5.

The tetracyclic compound (VI) is transformed to the corresponding methylamine (VII) by the process of EXAMPLE 6. The nature of this cleavage reaction depends on the particular $R_N$ attached to the tetracyclic compound (VI). This reaction is either a metal ammonia reduction or a metal catalyzed hydrogenolysis. This process opens the aziridine ring.

The methylamine (VII) is transformed to the desired (maleic) salt by the process of EXAMPLE 7.

The methylamine (VII), and its pharmaceutically acceptable salts, are known to be useful as a pharmaceutical agent in treating those individuals who have Parkinson's Disease, see U.S. Pat. No. 5,273,975.

It is preferred that the maleic salt (VII) be administered in the pharmaceutical dosage form describe in U.S. patent application Ser. No. 09/146,090.

The exact dosage and frequency of administration depends on the severity of the condition being treated, the age, weight, general physical condition of the particular patient, other medication the individual may be taking as is well known to those skilled in the art and can be more accurately determined by measuring the blood level or concentration of the methylamine (VI) and its metabolites in the patient's blood and/or the patient's response.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

Chemical formulas or portions thereof drawn in a linear fashion represent atoms in a linear chain. The symbol "—" in general represents a bond between two atoms in the chain. Thus $CH_3$—O—$CH_2$—$CH(R_i)$—$CH_3$ represents a 2-substituted-1-methoxypropane compound. In a similar fashion, the symbol "=" represents a double bond, e.g., $CH_2$=$C(R_i)$—O—$CH_3$, and the symbol "≡" represents a triple bond, e.g., HC≡ C—$CH(R_i)$—$CH_2$— $CH_3$. Carbonyl groups are represented in either one of two ways: —CO— or —C(=O)—, with the former being preferred for simplicity.

When a variable substituent is bivalent, the valences may be taken together or separately or both in the definition of the variable. For example, a variable $R_i$ attached to a carbon atom as —C(=$R_i$)— might be bivalent and be defined as oxo or keto (thus forming a carbonyl group (—CO—) or as two separately attached monovalent variable substituents I—$R_{i-j}$ and β-$R_{i-k}$. When a bivalent variable, $R_i$, is defined to consist of two monovalent variable substituents, the convention used to define the bivalent variable is of the form "I—$R_{i-j}$:β-$R_{i-k}$" or some variant thereof. In such a case both I—$R_{i-j}$ and β-$R_{i-k}$ are attached to the carbon atom to give —C(I—$R_{i-j}$)(β-$R_{i-k}$)—. For example, when the bivalent variable $R_6$, —C(=$R_6$)— is defined to consist of two monovalent variable substituents, the two monovalent variable substituents are I—$R_{6-1}$:β-$R_{6-2}$, ... I—$R_{6-9}$:β-$R_{6-10}$, etc, giving —C(I—$R_{6-1}$)(β-$R_{6-2}$)—, ... —C(I—$R_{6-9}$)(β-$R_{6-10}$)—, etc. Likewise, for the bivalent variable $R_{11}$, —C(=$R_{11}$)—, two monovalent variable substituents are I—$R_{11-1}$:β-$R_{11-2}$. For a ring substituent for which separate I and β orientations do not exist (e.g. due to the presence of a carbon carbon double bond in the ring), and for a substituent bonded to a carbon atom which is not part of a ring the above convention is still used, but the I and β designations are omitted.

Just as a bivalent variable may be defined as two separate monovalent variable substituents, two separate monovalent variable substituents may be defined to be taken together to form a bivalent variable. For example, in the formula —$C_1(R_i)$H—$C_2(R_j)$H—($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation ". . . $R_i$ and $R_j$ are taken together to form —$CH_2$— $CH_2$—O—CO— . . . " means a lactone in which the carbonyl is bonded to $C_2$. However, when designated ". . . $R_j$ and $R_i$ are taken together to form —CO—O—$CH_2$— $CH_2$— the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3$—$(CH_2)_n$—O— CO— where n is zero, one or two. By the second method the carbon atom content of only each portion of the definition is indicated separately by enclosing the "$C_i$-$C_j$" designation in parentheses and placing it immediately (no intervening space) before the portion of the definition being defined. By this optional convention ($C_1$-$C_3$)alkoxycarbonyl has the same meaning as $C_2$-$C_4$ alkoxy-carbonyl because the "$C_1$-$C_3$" refers only to the carbon atom content of the alkoxy group. Similarly while both $C_2$-$C_6$ alkoxyalkyl and ($C_1$-$C_3$) alkoxy($C_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

The compounds of formulas (I) thru (VIII) are a rigid cyclic (ring) structure and therefore defines an orientation with respect to the plane of the ring for substituents attached to each carbon atom of the rigid cyclic compound. Where the compounds have two substituents attached to a carbon atom, —C($X_1$)($X_2$)—, the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other relative to the viewer. In the chemical structural formulas (I) thru (VIII) of the invention depicting such compounds, a substituent ($X_1$) which is "below" another substituent ($X_2$) will be identified as being in the alpha (α) configuration and is identified by a broken, dashed or dotted line attachment to the carbon atom, i.e., by the symbol " - - - " or being in the beta (β) configuration and is indicated by an unbroken or solid line attachment to the carbon atom.

II. DEFINITIONS

All temperatures are in degrees Centigrade.

TLC refers to thin-layer chromatography.

HPLC refers to high pressure liquid chromatography.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

φ-refers to phenyl ($C_6H_5$).

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Preparation 1 (R)-Naproxen Chloride

R-naproxen (*Can. J. Chem.* 72(1). 142-5 (1994). 260 g), methylene chloride (3.33 kg) and DMF (8.2 ml) are added to a reactor. Oxalyl chloride (191.8 g) is slowly added to this mixture. After addition of the oxalyl chloride, the slurry is stirred at 5 to 10° and then slowly warmed to 20–25°. The resulting mixture is concentrated to remove the methylene chloride, branched octane is added to the concentrate and the mixture is again concentrated. More branched octane is added to the concentrate and the mixture is cooled to 0° and stirred to crystallize. The crystal slurry is filtered, the crystal cake is washed with octane and dried at 20–25° to obtain the title compound.

The filtrate from the first crop is concentrated, branched octane is added and the mixture is cooled and stirred to obtain a second crop of the title compound. The slurry is filtered, the crystal cake is washed with branched octane and dried at 20–25°.

Example 1

1-Benzyl-4H-imidazo[4,5,1-ij]quinolin-2(1H)-one (II)

A mixture of 4H-imidazo[4,5,1-ij]quinolin-2(1H)-one (I, *J. Heterocyclic Chem.*, 19, 837-49 (1982), 1.0 g, 5.8 mmol) in DMF (10 ml) is cooled to 0° and treated with potassium t-butoxide in THF (1.98 M, 3.2 ml, 6.3 mmol) maintaining the reaction temperature at 0°. The resulting mixture is stirred at 0° for 10 minutes. Benzyl bromide (0.73 ml, 6.1 mmol) is then added while maintaining the reaction temperature at methyl t-butyl ether (MTBE) from water followed by several water washes. The MTBE phase is concentrated under reduced pressure. The concentrate is cooled to 0°, filtered and washed two times with 0° MTBE. The product is dried at 50° under reduced pressure with a nitrogen purge to give the title compound, CMR ($CDCl_3$, 100 MHz) 153.78, 136.44, 128.69, 127.67, 127.60, 126.73, 125.86, 122.90, 122.78, 121.28, 116.92, 116.17, 108.36, 44.95 and 42.37 δ.

Example 2

(5R,6R)-1-benzyl-5-bromo-6-hydroxy-5,6-dihydro-4H-imidazo[4,5,1-ij]quinolin-2(1H)-one (III)

1-Benzyl-4H-imidazo[4,5,1-ij]quinolin-2(1H)-one (II, EXAMPLE 1, 240 g), acetonitrile (1.086 kg), water (227 ml) and fluoboric acid (48.5%, 13.4 g) are mixed and cooled to 0 to 5°. Dibromantin (163.5 g) is slurried into acetonitrile and is added to the reaction mixture. The reaction is carried out for about 3 hr at 0 to 5°. After the reaction is complete, methyl t-butyl ether is added over about 45 minutes keeping the reaction temperature in the pot below 10°. The slurry is cooled to −10 to −15°, stirred for an hour and then filtered. The product is washed with precooled methyl t-butyl ether, dried with 40° nitrogen to give the title compound, CMR ($CDCl_3$) δ156.0, 137.8, 130.5, 129.6, 129.3, 129.1, 126.6, 123.6, 122.5, 119.6, 110.4, 69.9, 49.6, 47.7, 46.9 and 43.8.

Example 3

(5S ,6S)-1-Benzyl-5-bromo-2-oxo-1,2,5,6-tetrahydro-4H-imidazo[4,5,1-ij]quinolin-6-yl (2R)-(6-methoxy-2-naphthyl)propanoate (IVA) and (5R,6R)-1-benzyl-5-bromo-2-oxo-1,2,5,6-tetrahydro-4H-imidazo[4,5,1-ij]quinolin-6-yl (2R)-(6-methoxy-2-naphthyl)propanoate (IVB)

(5R,6R)-1-Benzyl-5-bromo-6-hydroxy-5,6-dihydro-4H-imidazo[4,5,1-ij]quinolin-2(1H)-one (III, EXAMPLE 2, 143 g), methylene chloride (3,136 g), N-methyl morpholine (100.2 g) and 4-dimethylaminopyridine (497 mg) are added to the reactor and the mixture is cooled to 0 to 5°. (R)-Naproxen chloride (PREPARATION 1, 118.5 g) dissolved in methylene chloride (694 ml) is added to the reactor over about 1 hr and the mixture is stirred at 0 to 5° to complete the reaction. If necessary, additional naproxen chloride is added to complete the reaction. Potassium carbonate solution diluted with water is added to the mixture. The aqueous phase is extracted with methylene chloride and the combined methylene chloride phase is washed with water. The washed mixture is concentrated by vacuum distillation and solvent exchange with ethyl acetate is performed. The concentrate is cooled to −10° and stirred. The crystal slurry is filtered and the crystal cake is washed with precooled methyl t-butyl ether and dried at 50° to give the title compound in solid form, (5S,6S)-1-benzyl-5-bromo-2-oxo-1,2,5,6-tetrahydro-4H-imidazo[4,5,1-ij]quinolin-6-yl (2R)-2-(6-methoxy-2-naphthyl)propanoate (IVA), CMR (CDCl$_3$) δ173.2, 157.8, 153.4, 136.1, 134.6, 133.7, 129.2, 128.8, 127.8, 127.8, 127.6, 127.2, 125.9, 125.9, 125.6, 121.5, 121.4, 119.1, 113.2, 109.0, 105., 105.6, 69.2, 55.3, 45.4, 45.2, 42.5, 41.7 and 18.3.

The undesired isomer, (5R,6R)-1-benzyl-5-bromo-2-oxo-1,2,5,6-tetrahydro-4H-imidazo[4,5,1-ij]quinolin-6-yl (2R)-2-(6-methoxy-2-naphthyl)propanoate (IVB) is in the filtrate and can be recovered by means well known to those skilled in the art, (5R,6R)-1-benzyl-5-hydroxy-6-(methylamino)-5,6-dihydro-4H-imidazo[4,5,1-ij]quinolin-2(1H)-one, CMR (CDCl$_3$) 173.2, 157.9, 153.4, 136.1, 135.0, 133.8, 129.2, 128.9, 128.8, 127.8, 127.6, 127.4, 125.8, 125.8, 125.7, 121.6, 121.5, 119.3, 113.1, 109.1, 105.7, 68.7, 55.3, 45.3, 45.2, 42.2, 41.3 and 18.1 δ.

Example 4

(5R,6R)-1-benzyl-5-hydroxy-6-(methylamino)-5,6-dihydro-4H-imidazo[4,5,1-ij]quinolin-2(1H)-one (V)

(5S,6S)-1-Benzyl-5-bromo-2-oxo-1,2,5,6-tetrahydro-4H-imidazo[4,5,1-ij]quinolin-6-yl (2R)-2-(6-methoxy-2-naphthyl)propanoate (IVA, EXAMPLE 3, 110 g) is slurried in acetonitrile (1,297 g). After adding aqueous methylamine (40 wt %, 327 g) the reaction is carried out for about 12 hr at about 300. After the reaction is complete, the mixture is concentrated and ethyl acetate is added. Dilute hydrochloric acid is added to make the water-soluble salt of the title compound. The byproduct (R-naproxen methylamide impurity) is insoluble in water and stays in the ethyl acetate phase. Further extractions and washes are carried out for better separation of the (naproxen acetamide) impurity with minimum loss of the desired product. Then a sodium hydroxide solution is added to the aqueous phase and the hydrochloride salt of the title compound is converted to the free base. The free base is less soluble in water and is extracted into ethyl acetate. The product mixture is concentrated and solvent exchanged with ethyl acetate to remove water. Crystallization is performed by adding branched chain octane and cooling the mixture. The resulting slurry is filtered, washed and dried at 50° to give the title compound, CMR (CDCl$_3$) δ153.7, 136.3, 128.7, 127.8, 127.7, 125.7, 121.3, 119.9, 118.6, 107.5, 66.2, 60.1, 45.1, 42.6 and 34.0.

Example 5

(7aS,8aR)-4-benzyl-8-methyl-7,7a,8,8a-tetrahydroazireno[2,3-c]imidazo[4,5,1-ij]quinolin-5(4H)-one (VI)

(5R,6R)-1-benzyl-5-hydroxy-6-(methylamino)-5,6-dihydro-4H-imidazo[4,5,1-ij]quinolin-2(1H)-one (V, EXAMPLE 4, 70 g) and THF (1,389 g) is concentrated to remove any by distillation as a precaution due to reactivity of n-butyllithium towards water. The mixture is cooled to about −10° and n-butyllithium is added to make the lithium salt of the starting material with formation of n-butane byproduct in an exothermic reaction. Benzenesulfonyl chloride is added slowly to make benzenesulfonate in an exothermic reaction. The reaction mixture is warmed to 20–25° to complete the reaction. Agueous potassium carbonate solution is added to scavenge the benzenesulfonic acid and the mixture is stirred to allow crystallization. Water is added to complete crystallization, the slurry is stirred, cooled and filtered. The crystal cake is washed with water followed by branched chain octane and dried at 40 to 50° to give the title compound, CMR (CDCl$_3$) δ154.1, 136.3, 128.6, 127.9, 127.6, 124.3, 120.7, 119.7, 107.4, 46.7, 44.9, 40.7, 38.1 and 37.6.

Example 6

(5R)-(methylamino)-5,6-dihydro-4H-imidazo[4,5,1-ij]quinolin-2(1H)-one (VII)

A mixture of (7aS,8aR)-4-benzyl-8-methyl-7,7a,8,8a-tetrahydroazireno[2,3-c]imidazo[4,5,1-ij]quinolin-5(4H)-one (VI, EXAMPLE 5,40 g) t-amyl alcohol (42.4 g) and anhydrous ammonia (1,200 g) is treated with lithium at −33°. After the lithium addition is complete, the reaction mixture changes from a yellow slurry to a dark blue mixture. This dark blue mixture is stirred for 30–60 minutes and then quenched with the addition of water. The cooling is removed from the condenser and the ammonia is allowed to evaporate. The residue is dissolved in methanol. This mixture is then concentrated to dryness to give the title compound, which is carried on directly to the next step without isolation.

Example 7

(5R)-(methylamino)-5,6-dihydro-4H-imidazo[4,5,1-ij]quinolin-2(1H)-one (Z)-2-butenedioate (1:1) (VIII)

(5R)-(methylamino)-5,6-dihydro-4H-imidazo[4,5,1-ij]quinolin-2(1H)-one (VII, EXAMPLE 6, 28.0 g) is dissolved in water and the pH is adjusted to 10 with the addition of hydrochloric acid. The mixture is applied in portions to an XAD-16 resin column which is eluted first with water and then with ethanol. The inorganic salts are eluted from the column first with the desired product eluted with the ethanol. The ethanol eluate from the column is treated with maleic acid and the water level is lowered through azeotropic distillation of the ethanol. The precipitated product is isolated by filtration, rinsed with ethyl acetate and dried to give the title compound, CMR (DMSO-d$_6$) δ167.6, 153.9, 136.4, 127.1, 121.5, 119.6, 114.1, 107.5, 51.9, 31.3 and 26.5.

CHART A

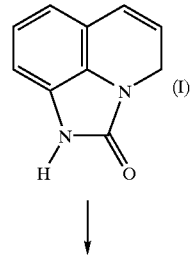

-continued

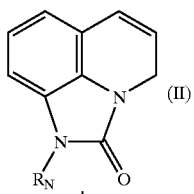
(II)

↓

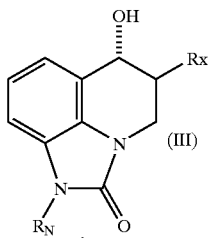
(III)

↓

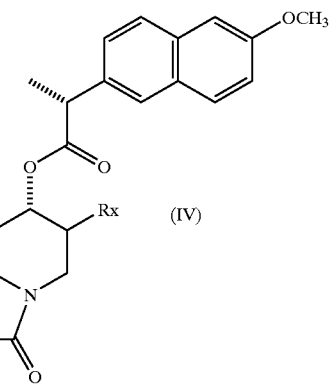
(IV)

↓

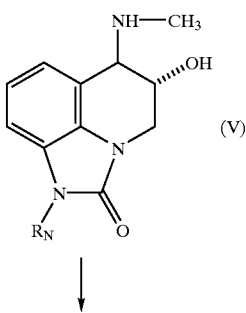
(V)

↓

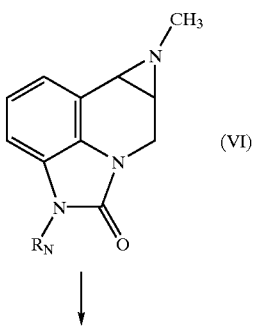
(VI)

↓

-continued

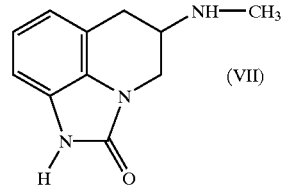
(VII)

↓

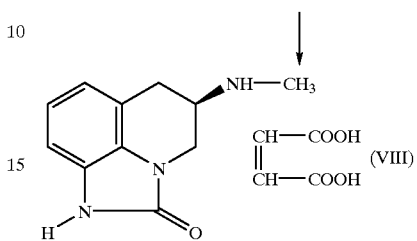
(VIII)

What is claimed is:

1. A process for the preparation of a tetracyclic compound of formula (VI)

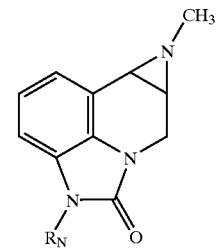

where $R_N$ is selected from the group consisting of:

(A) φ-CH$_2$— where phenyl is optionally substituted with 1 or 2:
  (1) $C_1$-$C_4$ alkoxy,
  (2) F—,
  (3) Cl—,
  (4) Br—,
  (5) I—,
  (6) $C_1$-$C_4$ alkyl, (B) $R_{N1}$—CH$_2$—O—CH$_2$ where $R_{N1}$ is selected from the group consisting of:
  (1) φ-optionally substituted with:
    (a) $C_1$-$C_4$ alkyl,
    (b) F—,
    (c) Cl—,
    (d) Br—,
    (e) I—,
    (f) $C_1$-$C_4$ alkoxy,
  (2) (CH$_3$)$_3$Si—CH$_2$—,
  (3) $R_{N2}$—O—CH$_2$— where $R_{N2}$ is $C_1$-$C_4$ alkyl,
  (4) CH$_2$=CH—,
  (5) —H,
  (6) $C_1$-$C_4$ alkyl;

(C) an unsaturated compound selected from the group consisting of:
  (1) CH$_2$=CH—CH$_2$—,
  (2) CH$_3$—CH=CH—CH$_2$—,
  (3) φ—CH=CH—CH$_2$— which comprises:

(1) contacting a hydroxy-amino compound of formula (V),

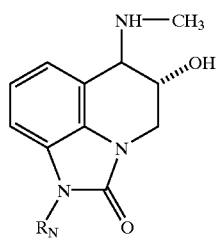

where $R_N$ is as defined above, with strong base, (2) contacting the reaction mixture of step (1) with a compound of the formula $R_S$—$SO_2$—X where $R_S$ is phenyl or substitute phenyl and where X is —Cl and —Br and (3) contacting the reaction mixture of step (2) with a weak base.

2. A process according to claim 1 where the strong base is selected from the group consisting of butyllithium, methyllithium, potassium hexamethyldisilazide and lithium diisopropylamide.

3. A process according to claim 2 where the strong base is butyllithium.

4. A process according to claim 1 where $R_S$ is phenyl or tolyl.

5. A process according to claim 1 where the weak base is selected from the group consisting of bicarbonate, carbonate, phosphate buffers and hydroxide.

6. A process according to claim 5 where the weak base is bicarbonate.

* * * * *